United States Patent [19]
Lindegren et al.

[11] Patent Number: 5,454,837
[45] Date of Patent: Oct. 3, 1995

[54] IMPLANTABLE MEDICAL SYSTEM WITH OPTICAL COMMUNICATION BETWEEN A TREATMENT SITE AND A THERAPY-GENERATING APPARATUS

[75] Inventors: Ulf Lindegren, Enskede, Sweden; Modesto Guerola, Barcelona, Spain

[73] Assignee: Pacesetter AB, Solna, Sweden

[21] Appl. No.: 241,398

[22] Filed: May 11, 1994

[30] Foreign Application Priority Data

Jun. 1, 1993 [SE] Sweden ................................. 9301855

[51] Int. Cl.⁶ ........................................................ A61N 1/36
[52] U.S. Cl. ........................... 607/9; 607/4; 607/63; 128/908
[58] Field of Search ....................... 128/908; 607/2, 607/4, 9, 32, 33, 63

[56] References Cited

U.S. PATENT DOCUMENTS

| | | | |
|---|---|---|---|
| 4,041,954 | 8/1977 | Ohara | 128/905 |
| 4,254,771 | 3/1981 | Tanie et al. | 607/63 |
| 4,432,363 | 2/1984 | Kakegawa | 607/33 |
| 4,807,632 | 2/1989 | Liess et al. | 128/634 |
| 4,815,469 | 3/1989 | Cohen et al. | 128/634 |
| 5,058,586 | 10/1991 | Heinze | 607/125 |

*Primary Examiner*—William E. Kamm
*Attorney, Agent, or Firm*—Hill, Steadman & Simpson

[57] ABSTRACT

An implantable medical system, having an implanted therapy-generating apparatus which administers a medical therapy in vivo to a treatment site remote from the therapy-generating apparatus, includes at least one optical conductor connected between the therapy-generating apparatus and the tissue at the treatment site, or an additional implantable medical device. Energy and/or information can be transmitted by optical signals using the optical conductor, in a safe and noise-free manner. Each location at which the optical signals are to be transmitted or received is provided with an optoelectrical converter, or an electro-optical converter, as appropriate.

46 Claims, 2 Drawing Sheets

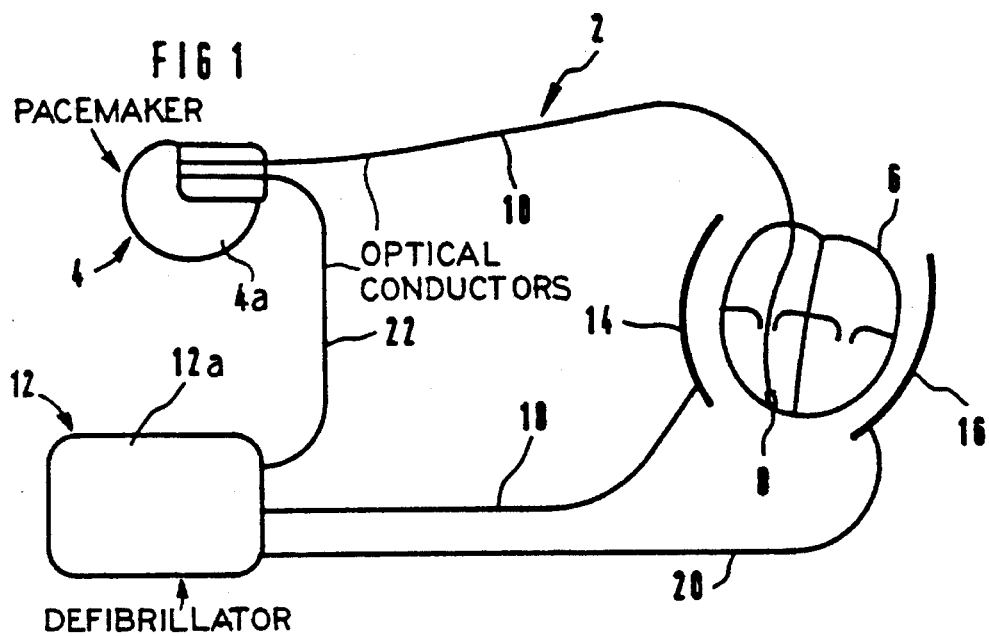
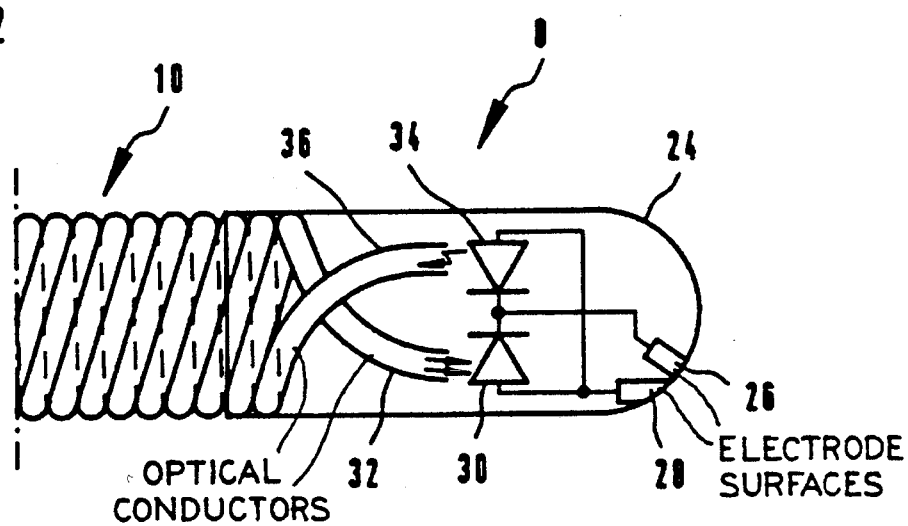

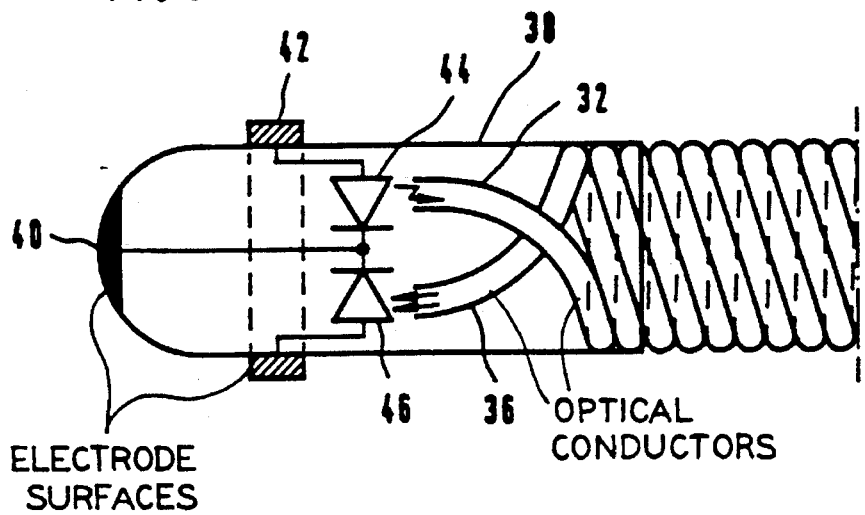
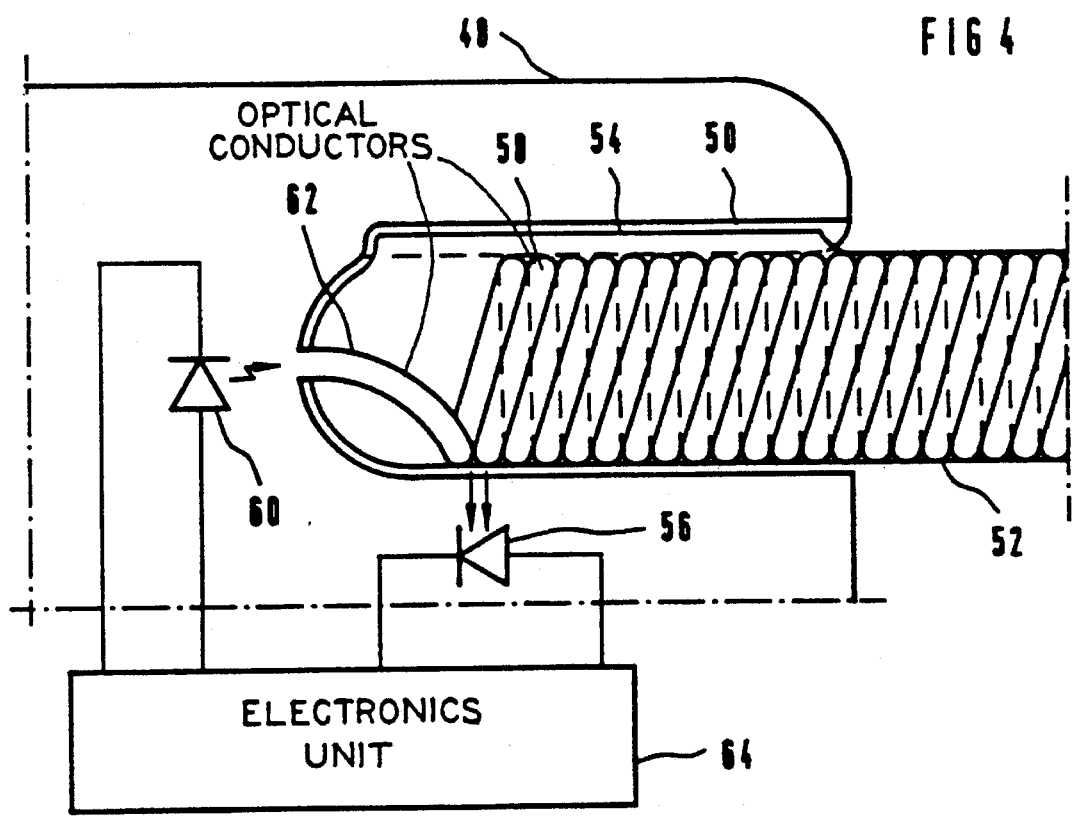

IMPLANTABLE MEDICAL SYSTEM WITH OPTICAL COMMUNICATION BETWEEN A TREATMENT SITE AND A THERAPY-GENERATING APPARATUS

BACKGROUND OF THE INVENTION

1. Field of the Invention

The present invention is directed to an implantable medical system, for administering therapy in vivo to living tissue, of the type including an implantable therapy-generating apparatus connected to a treatment site remote from the apparatus, as well as to such a medical system having at least two separate implantable therapy-generating apparatus, with the capability of communicating between the two implanted apparatuses.

2. Description of the Prior Art

Many types of implantable medical devices, such as pacemakers and defibrillators, are employed in systems for connection to living tissue for sensing tissue functions or for treating the tissue. The devices can be implantable or extracorporeal. The devices are connected to the living tissue by metallic conductors. A plurality of such devices can be used in a single system, each device being connected to the living tissue, and the implanted devices being interconnected with metallic conductors so that information can be exchanged between the devices.

Metallic leads can cause problems, particularly in implanted systems. A conductor used to transmit pacemaker pulses between a pacing pulse generator and a treatment site may, for example, pick up a defibrillation pulse generated by another device, thereby resulting in a spurious detection of cardiac activity, and may also damage the pacemaker electronics. The metallic conductors are usually contained in an insulating sheath made of a polymer, such as silicone, to keep the leads from having any effect on the surrounding tissue which is not to be sensed or stimulated. The requirement for such an insulating sheath means that the lead cannot be made as thin as is desirable.

SUMMARY OF THE INVENTION

It is an object of the present invention to provide a medical system of the type described above wherein the number of metallic conductors is minimized.

Such a medical system is achieved in accordance with the principles of the present invention by employing at least one optical conductor having a proximal end connected to a therapy-generating device and a distal end which is disposed at a location remote from the therapy-generating apparatus. A first converter or transducer is disposed at the proximal end of the optical conductor for converting optical signals into electrical signals and/or for converting electrical signals into optical signals. A second converter is located at the distal end of the optical conductor, for converting optical signals into electrical signals and/or for converting electrical signals into optical signals. A further component of the medical system is disposed at the distal end of the optical conductor, and receives and/or transmits signals to and/or from the therapy-generating apparatus via the optical conductor. The further component may be an electrode for administering therapy in the form of electrical energy to tissue at the treatment site, or may be a sensor for obtaining physiological information about tissue in the region of the treatment site, or may be a further medical device, such as another therapy-generating apparatus, with information being exchanged between the therapy-generating apparatus and the further therapy-generating apparatus.

By employing an optical conductor for carrying signals and/or energy, metallic conductors are not needed for most connections between medical a therapy-generating apparatus and living tissue, or between different medical devices.

The component disposed at the distal end of the optical conductor may include a first electrode surface and a second electrode surface, both connected to the second converter, so that electrical signals generated by the second converter are delivered to the living tissue via the first electrode surface as well as via the second electrode surface.

The system of the invention may be employed, for example, for delivering stimulation pulses to a heart, and would thus replace known electrode systems for pacemakers employing metallic conductors. For this purpose, the pacing electronics of the pacemaker would supply an electrical signal to the first converter located at the proximal end of the optical conductor, which would then be converted into a light pulse which would be transmitted via the optical conductor to the second converter located at the distal end. The second converter would then convert the optical pulse into an electrical pulse for stimulating the tissue.

Alternatively, or in addition to the above example, the first and second electrode surfaces disposed at the distal end of the optical conductor and connected to the second converter may be employed as a sensor, so that electrical signals sensed between the first electrode surface and the second electrode surface are supplied to the second converter, which generates an optical signal which is transmitted to the first converter via the optical conductor. The optical signal is then converted into an electrical signal and is appropriately analyzed in a known manner.

This embodiment permits living tissue to be sensed without the use of metallic conductors. If a combination of the above two embodiments is used in the context of a pacemaker, a heart can therefore be stimulated and sensed without the use of any metallic conductors whatsoever. The component connected at the distal end of the optical conductor may additionally include a third electrode surface and a fourth electrode surface, both connected to the second converter, so that electrical signals sensed between the third electrode and fourth electrode surfaces can be supplied to the second converter to generate an optical signal which is transmitted to the first converter via the optical conductor. With two pairs of electrode surfaces, one pair can be used exclusively for emitting stimulation pulses, and the other pair can be used exclusively for sensing. The system can then include means for automatically checking as to whether an emitted stimulation pulse has achieved a desired effect, i.e., whether it induces an appropriate tissue response.

Preferably, the distance between the electrode surfaces in a pair of electrodes is less than 2 mm.

With a short distance between the electrode surfaces in a pair, the current needed to stimulate tissue would not have to be very high in order to depolarize one or several cardiac tissue cells, which would be sufficient to initiate a depolarization wave which stimulates all of the cardia tissue.

In a further embodiment of the invention, the component connected at the distal end of the optical conductor is an additional medical device, and information is transmittable between this additional medical device and the aforementioned therapy-generating apparatus via the optical conductor.

Particularly in implantable systems utilizing a plurality of devices, it is advantageous if information transmission between the devices is as free of noise as possible. This is achieved in accordance with the invention by the use of optical signals, which are unaffected by electromagnetic fields in the environment, thereby making the information transfer more reliable.

As used herein the term "implantable system" refers to a system which includes at least some components which are implantable, but does not necessarily require that all components of this system be implantable. An "implantable system" may include one or more extracorporeal components.

DESCRIPTION OF THE DRAWINGS

FIG. 1 is a schematic illustration of an embodiment of a medical system constructed in accordance with the principles of the present invention.

FIG. 2 shows an enlarged, detailed view of a tip electrode for stimulating and sensing heart tissue constructed in accordance with the principles of the present invention.

FIG. 3 shows a detailed, enlarged view of a contact plug for connection to a pacemaker or a defibrillator, constructed in accordance with the principles of the present invention.

FIG. 4 shows a detailed, enlarged view of a further embodiment of a connection for an optical conductor to a pacemaker or a defibrillator, constructed in accordance with the principles of the present invention.

DESCRIPTION OF THE PREFERRED EMBODIMENTS

A medical system 2, shown in FIG. 1, includes a pacemaker 4 connected to a heart 6 by an electrode element 8. The pacemaker 4 has a housing 4a of a size permitting implantation in the body of a subject. The electrode element 8 and the pacemaker 4 are connected to each other by means of a first optical line 10, which carries signals and energy between the pacemaker 4 and the electrode element 8. Heart tissue can be sensed, or induced to trigger a heartbeat, via the electrode element 8. The medical system 2 also includes a defibrillator 12, which is also connected to the heart 6. The defibrillator 6 has a housing 6a of a size permitting implantation in the body of the subject. A first defibrillation electrode 14 and a second defibrillation electrode 16 are positioned so as to surround the heart 6. The defibrillation electrodes 14 and 16 are connected to the defibrillator 12 by respective first and second metallic conductors 18 and 20. If the heart 6 exhibits fibrillation, The heart 6 can be defibrillated by means of the defibrillator 12 delivering a defibrillation pulse across the first defibrillation electrode 14 and the second defibrillation electrode 16. The pacemaker 4 and the defibrillator 12 are interconnected by a second optical line 22, so those components can exchange information.

FIG. 2 shows the structure of an exemplary embodiment of the electrode element 8 in greater detail. The electrode element 8 includes an electrode body 24, preferably made of a biocompatible polymer or another type of electrically insulating material. A first electrode surface 26 and a second electrode surface 28 are disposed at the exterior of the electrode body 24. The electrode surfaces 26 and 28 are positioned close to each other, for example, at a distance of 0.5 mm. This reduces the stimulation energy needed to trigger a heartbeat. A photodiode 30 is electrically connected to both of the electrode surfaces 26 and 28. The photodiode 30 is positioned so that optical signals, carried by a first optical conductor 32 in the optical lead 10, are incident on the photodiode 30 and are converted therein into pulses of electrical energy. These energy pulses are delivered to surrounding tissue via the first electrode surface 26 and the second electrode surface 28. A light-emitting diode 34 is also disposed in the electrode body 24. The light-emitting diode 34 emits light signals when electrical signals arising in the heart tissue are picked-up by the first electrode surface 26 and the second electrode surface 28. These generated optical signals are incident on an end face of a second optical conductor 36 contained in the optical line 10. The first optical conductor 32 and the second optical conductor 36 may be interleaved to form a helical coil, which proceeds the length of the first optical line 10. If the optical conductors 32 and 36 are made of a biocompatible, optical polymer, they can be helically coiled with a very small diameter, thereby making the first optical line 10 thinner than a corresponding metallic conductor contained in an insulating sheath.

A contact plug 38 is shown in FIG. 3, which is intended for detachable connection of the optical conductors 32 and 36 to the pacemaker 4. The contact plug 38 has a first contact surface 40 and a second contact surface 42 which are both in electrical contact with pacemaker electronics (not shown). A light-emitting diode 44 is connected across the first contact surface 40 and the second contact surface 42, so that it emits optical signals onto an end face of the first optical conductor 32, which are transmitted along the first optical conductor 32. A photodiode 46 is disposed to receive optical signals carried by the second optical conductor 36, and converts the received signals into electrical signals.

FIG. 4 shows an alternative structure for achieving contact between the optical conductors and the remainder of the medical device. In this embodiment, a contact socket 48, which may be present as part of the pacemaker 4 and/or as part of the defibrillator 12, has a receiver receptacle 50, into which a contact plug 52 can be inserted. The contact plug 52 has a guide key 54, in the form of a ridge or projection, to ensure correct insertion of the contact plug 52 into the receiver receptacle 50. Within the contact socket 48, a photodiode 56 is disposed to receive the optical signals carried by a first optical conductor 58. A light-emitting diode 60 is also disposed in the contact socket 48, which emits optical signals to be carried by a second optical conductor 62. The photodiode 56 and the light-emitting diode 60 are connected to an electronics unit 64 which may be, for example, the pacemaker electronics or the defibrillator electronics.

Although further modifications and changes may be suggested by those skilled in the art, it is the intention of the inventors to embody within the patent warranted hereon all changes and modifications as reasonably and properly come within the scope of their contribution to the art.

We claim as our invention:

1. An medical system for implantation in a body containing body tissue comprising:

an implantable housing containing therapy-generating means for generating electrical signals;

an implantable optical conductor having a first end and a second end;

means for attaching said first end of said optical conductor to said therapy-generating means;

implantable electrical means for in vivo electrically interacting with said body tissue;

means for attaching said electrical means to said second end of said optical conductor;

first converter means disposed at said first end of said optical conductor for converting said electrical signals into corresponding optical signals, said optical signals being transmitted by said optical conductor to said second end of said optical conductor; and second converter means disposed at said second end of said optical conductor for converting said optical signals into corresponding electrical signals supplied to said electrical means.

2. A system as claimed in claim 1 further comprising a lead containing said optical conductor and having a proximate end and a distal end, wherein said electrical means includes a first electrode surface and a second electrode surface of said lead, wherein said means for attaching said first end of said optical conductor to said therapy-generating means comprise means for attaching both said first end of said optical conductor and said proximate end of said lead to said therapy-generating means, and wherein said means for attaching said electrical means to said second end of said optical conductor comprise means for mounting said first and second electrode surfaces at an exterior of said distal end of said lead with said first and second electrode surfaces electrically connected to said second converter means, and said electrical means, including said first and second electrode surfaces, forming means for delivering said corresponding electrical signals to said body tissue.

3. A system as claimed in claim 2 wherein said first and second electrode surfaces are spaced apart by a distance which is less than 2 mm.

4. A system as claimed in claim 1 wherein said first converter means comprise a light-emitting diode.

5. A system as claimed in claim 1 wherein said first converter means comprise a laser diode.

6. A system as claimed in claim 1 wherein said second converter means comprise a photodiode.

7. A system as claimed in claim 1 wherein said means for attaching said first end of said optical conductor to said therapy-generating means comprises means for detachably connecting said first end of said optical conductor and said therapy-generating means.

8. A system as claimed in claim 7 wherein said first converter means is an integral part of said means for detachably connecting.

9. A system as claimed in claim 1 wherein said electrical means comprises an additional therapy generating means for generating additional electrical signals, contained in an additional housing.

10. A system as claimed in claim 9 wherein said means for attaching said electrical means to said second end of said optical conductor comprises means for detachably connecting said second end of said optical conductor and said additional therapy-generating means.

11. A system as claimed in claim 10 wherein said second converter means is an integral part of said means for detachably connecting.

12. A system as claimed in claim 9:

wherein said means for attaching said first end of said optical conductor to said therapy-generating means comprises first means for detachably connecting said first end of said optical conductor and said therapy-generating means; and wherein said means for attaching said second end of said optical conductor to said electrical means comprises second means for detachably connecting said second end of said optical conductor and said additional therapy-generating means.

13. A system as claimed in claim 12 wherein said first converter means is an integral part of said first means for detachably connecting and wherein said second converter means is an integral part of said second means for detachably connecting.

14. A system as claimed in claim 1 wherein said optical conductor is helically coiled.

15. An implantable medical system comprising:

therapy-generating means contained in an implantable housing for administering medical therapy dependent n a physiological condition of said subject;

an implantable optical conductor having a first end and a second end;

means for attaching said first end of said optical conductor to said therapy-generating means;

implantable electrical means for in vivo electrically interacting with said subject for generating electrical signals resulting from the interaction which represent said physiological condition;

means for attaching said electrical means to said second end of said optical conductor;

first converter means, disposed at said second end of said optical conductor, for converting said electrical signals generated by said electrical component into corresponding optical signals, said optical signals being transmitted by said optical conductor to said first end of said optical conductor; and second converter means disposed at said first end of said optical conductor for converting said optical signals into corresponding electrical signals representing said physiological condition supplied to said therapy-generating means for use in administering said therapy.

16. A system as claimed in claim 15 further comprising a lead containing said optical conductor and having a proximate end and a distal end, wherein said electrical means include a first electrode surface and a second electrode surface of said lead, wherein said means for attaching said first end of said optical conductor to said therapy-generating means comprise means for attaching both said first end of said optical conductor and said proximate end of said lead to said therapy-generating means, and wherein said means for attaching said electrical means to said second end of said optical conductor comprise means for mounting said first and second electrode surfaces at an exterior of said distal end of said lead with said first and second electrode surfaces electrically connected to said first converter means, said electrical means, including said first and second electrode surfaces, forming means for sensing electrical activity in body tissue and for generating said electrical signals resulting from said interaction as sensor signals corresponding to said electrical activity.

17. A system as claimed in claim 16 wherein said first and second electrode surfaces are spaced apart by a distance which is less than 2 mm.

18. A system as claimed in claim 15 wherein said first converter means comprise a light-emitting diode.

19. A system as claimed in claim 15 wherein said first converter means comprise a laser diode.

20. A system as claimed in claim 15 wherein said second converter means comprise a photodiode.

21. A system as claimed in claim 15 wherein said means for attaching said first end of said optical conductor to said therapy-generating means comprises means for detachably connecting said first end of said optical conductor and said therapy-generating means.

22. A system as claimed in claim 21 wherein said first converter means is an integral part of said means for detachably connecting.

23. A system as claimed in claim 15 wherein said electrical means comprises an additional therapy generating means for generating additional electrical signals, contained in an additional housing.

23. A system as claimed in claim 23 wherein said means for attaching said electrical means to said second end of said optical conductor comprises means for detachably connecting said second end of said optical conductor and said additional therapy-generating means.

25. A system as claimed in claim 24 wherein said second converter means is an integral part of said means for detachably connecting.

26. A system as claimed in claim 23:
   wherein said means for attaching said first end of said optical conductor to said therapy-generating means comprises first means for detachably connecting said first end of said optical conductor and said therapy-generating means; and
   wherein said means for attaching said second end of said optical conductor to said electrical means comprises second means for detachably connecting said second end of said optical conductor and said additional therapy-generating means.

27. A system as claimed in claim 26 wherein said first converter means is an integral part of said first means for detachably connecting and wherein said second converter means is an integral part of said second means for detachably connecting.

28. A system as claimed in claim 15 wherein said optical conductor is helically coiled.

29. An implantable medical system for implantation in a body, comprising:
   an implantable housing containing therapy-generating means for emitting first electrical signals dependent on a physiological condition of said body and for receiving second electrical signals representing said physiological condition;
   an optical conductor having a first end and a second end;
   means for connecting said first end of said optical conductor to said therapy-generating means;
   implantable electrical means for in vivo interacting with said body and including means for receiving said first electrical signals and for generating said second electrical signals;
   means for connecting said electrical means to said second end of said optical conductor;
   first converter means disposed at said first end of said optical conductor for converting said first electrical signals into first optical signals, said first optical signals being transmitted by said optical conductor to said second end of said optical conductor;
   second converter means disposed at said second end of said optical conductor for converting said first optical signals into corresponding electrical signals supplied to said electrical means;
   third converter means disposed at said second end of said optical conductor for converting said second electrical signals into said second optical signals, said second optical signals being transmitted by said optical conductor to said first end of said optical conductor; and
   fourth converter means disposed at said first end of said optical conductor for converting said second optical signals into corresponding electrical signals supplied to said therapy-generating means for use in emitting said first electrical signals.

30. A system as claimed in claim 29 further comprising a lead containing said optical conductor and having a proximate end and a distal end, wherein said electrical means includes a first electrode surface and a second electrode surface of said lead, wherein said means for attaching said first end of said optical conductor to said therapy-generating means comprise means for attaching both said first end of said optical conductor and said proximate end of said lead to said therapy-generating means, and wherein said means for attaching said electrical means to said second end of said optical conductor comprise means for mounting said first and second electrode surfaces at an exterior of said distal end of said lead with said first and second electrode surfaces electrically connected to said second converter means, and said electrical means including said first and second electrode surfaces, forming means for delivering said electrical signals corresponding to said first optical signal to said body.

31. A system as claimed in claim 30 wherein said first and second electrode surfaces are spaced a distance apart which is less than 2 mm.

32. A system as claimed in claim 29 further comprising a lead containing said optical conductor and having a proximate end and a distal end, wherein said electrical means includes first and second electrode surfaces on said lead, wherein said means for attaching said first end of said optical conductor to said therapy-generating means comprise means for attaching both said first end of said optical conductor and said proximate end of said lead to said therapy-generating means, and wherein said means for attaching said electrical means to said second end of said optical conductor comprise means for mounting said first and second electrode surfaces at an exterior of said distal end of said lead with said first and second electrode surfaces electrically connected to said third converter means, and said electrical means including said first and second electrode surfaces, forming means for sensing electrical activity in tissue and for generating said second electrical signal as a sensor signal corresponding to said electrical activity.

33. A system as claimed in claim 32 wherein said first and second electrode surfaces are disposed a distance apart which is less than 2 mm.

34. A system as claimed in claim 29 further comprising a lead containing said optical conductor and having a proximate end and a distal end, wherein said electrical means includes a first electrode surface, a second electrode surface, a third electrode surface and a fourth electrode surface on said lead, wherein said means for attaching said first end of said optical conductor to said therapy-generating means comprise means for attaching both said first end of said optical conductor and said proximate end of said lead to said therapy-generating means, and wherein said means for attaching said electrical means to said second end of said optical conductor comprise means for mounting said first and second electrode surfaces at an exterior of said distal end of said lead with said first and second electrode surfaces electrically connected to said second converter means and said third and fourth electrode surfaces electrically connected to said third converter means, said first and second electrode surfaces forming means for delivering said electrical signal corresponding to said first optical signal to said body, and said third and fourth electrode surfaces means for sensing electrical activity in said body and for generating said second electrical signal as a sensor signal corresponding to said electrical activity.

35. A system as claimed in claim 34 wherein said first and second electrode surfaces are disposed a distance apart which is less than 2 mm, and wherein said third and fourth electrode surfaces are disposed a distance apart which is less than 2 mm.

36. A system as claimed in claim 29 wherein said first converter means and said third converter means each comprise a light-emitting diode.

37. A system as claimed in claim 29 wherein said converter means and said third converter means each comprise a laser diode.

38. A system as claimed in claim 29 wherein said second converter means and said fourth converter means each comprise a photodiode.

39. A system as claimed in claim 29 wherein said means for attaching said first end of said optical conductor to said therapy-generating means comprises means for detachably connecting said first end of said optical conductor and said therapy-generating means.

40. A system as claimed in claim 39 wherein said first converter means is an integral part of said means for detachably connecting.

41. A system as claimed in claim 29 wherein said electrical means comprises an additional therapy generating means for generating additional electrical signals, contained in an additional housing.

42. A system as claimed in claim 40 wherein said means for attaching said electrical means to said second end of said optical conductor comprises means for detachably connecting said second end of said optical conductor and said additional therapy-generating means.

43. A system as claimed in claim 42 wherein said second converter means is an integral part of said means for detachably connecting.

44. A system as claimed in claim 41:

wherein said means for attaching said first end of said optical conductor to said therapy-generating means comprises first means for detachably connecting said first end of said optical conductor and said therapy-generating means; and wherein said means for attaching said electrical means to said second end of said optical conductor comprises second means for detachably connecting said second end of said optical conductor and said additional therapy-generating means.

45. A system as claimed in claim 44 wherein said first converter means is an integral part of said first means for detachably connecting and wherein said second converter means is an integral part of said second means for detachably connecting.

46. A system as claimed in claim 29 wherein said optical conductor is helically coiled.

* * * * *